United States Patent [19]

Severin et al.

[11] Patent Number: 4,787,904

[45] Date of Patent: Nov. 29, 1988

[54] HYDROPHILLIC INTRAOCULAR LENS

[76] Inventors: Sanford L. Severin, 1313 Solano Ave., Albany, Calif. 94706; Carl S. Johnson, 61 Sugarloaf La., Alamo, Calif. 94570

[21] Appl. No.: 628,431

[22] Filed: Jul. 6, 1984

[51] Int. Cl.⁴ .............................................. A61F 2/16
[52] U.S. Cl. .................................... 623/6; 128/303 R
[58] Field of Search ........................ 3/13; 351/160 H; 128/76.5, 303 R; 623/6

[56] References Cited

U.S. PATENT DOCUMENTS

| | | | |
|---|---|---|---|
| 2,834,023 | 5/1958 | Lieb | 3/13 |
| 4,473,910 | 10/1984 | Grinder | 623/6 |
| 4,502,162 | 3/1985 | Gerhard et al. | 623/6 |
| 4,521,254 | 6/1985 | Anderson | 134/26 |
| 4,556,998 | 10/1985 | Siepser | 623/6 |
| 4,573,998 | 3/1986 | Mazzocco | 623/6 |
| 4,578,078 | 3/1986 | Arkell et al. | 623/6 |
| 4,588,405 | 5/1986 | Knolle, Jr. | 623/6 |

Primary Examiner—Mark L. Bell
Attorney, Agent, or Firm—John J. Leavitt; George M. Cooper

[57] ABSTRACT

Presented is an intraocular lens structure fabricated from a material that is hydrophilic, which is sufficiently flexible when hydrated to be rolled or bent into a compact formation for insertion into the eye through a much smaller than usual incision or opening, and which may be implanted either in the capsular bag from which the natural lens has been aspirated, or which may be supported in the posterior chamber sulcus, or in the anterior chamber angle. The lens structure, in one aspect of the invention, is specially packed in a tubular container that retains the hydrated lens structure conformed into a minimum diameter configuration for ease of delivery into the eye, and which, in another aspect of the invention, embodies a package that includes means for delivering the hydrated lens into the eye.

41 Claims, 3 Drawing Sheets

HYDROPHILLIC INTRAOCULAR LENS

BACKGROUND OF THE INVENTION

1. Field of the Invention

This invention relates to implantable intraocular lenses, and particularly to an intraocular lens structure fabricated from an optically transparent hydrophilic material which may be rolled or bent into a compact configuration for packaging and delivery into the eye.

2. Description of the Prior Art

We are unaware of any prior art relating specifically to implantable intraocular lens structures that are hydrophilic to the point that they are "soft" in the sense that the hydrated lens structure may be rolled or bent into a compact form for storage, retained in that form during delivery into the eye, and extended into its final form after delivery into the eye.

Accordingly, it is one of the important objects of the present invention to provide an implantable intraocular lens structure that is fabricated from a hyrophilic material that may be hydrated prior to delivery into the eye.

Another object of the invention is the provision of a hydrophilic intraocular lens structure that may be delivered into the eye in either a hydrated or dehydrated condition.

Still another object of the invention is the provision of an intraocular hydrophilic and hydrated lens structure that may be rolled or bent into a compact tubular form for delivery into the eye, with subsequent extension of the lens assembly into its normal form.

A still further object of the invention is the provision of a hydrated hydrophilic intraocular lens structure for implantation in the posterior or anterior chamber of the eye, which may be conformed prior to delivery into a conformation permitting its delivery through a smaller than usual opening in the order of about 3.5 mm as compared to the 6.5 mm opening usually required.

Yet another object of the invention is the provision of an implantable intraocular lens assembly, including the lens body and the supporting loops, which is packaged in a manner that enables the package to function as part of the delivery means.

Intraocular lens structures are by their very nature extremely small in size, delicate, susceptible to being damaged, and therefore difficult to package and store in a sterile condition. Accordingly, it is another object of the invention to provide a means for packaging intraocular lens assemblies of hydrated hyrophilic material which facilitates storing in a sterile hydrated condition and which facilitates delivery of the lens into the eye of the patient.

The invention possesses other objects and features of advantage, some of which, with the foregoing, will be apparent from the following description and the drawings. It is to be understood however that the invention is not limited to the embodiment illustrated and described since it may be embodied in various forms within the scope of the appended claims.

SUMMARY OF THE INVENTION

In terms of broad inclusion, the hydrophilic intraocular lens assembly of the invention comprises an optically transparent lens body having a predetermined transverse dimension defining an outer periphery disposed about a central axis, and a plurality of support members, preferably in the form of crescentiform loops, extending from the periphery of the lens body and adapted to support the lens assembly within the eye. The lens body is formed from a hydrophilic synthetic resin material formulated to accept hydration to the point that it will accommodate non-planar conformation of the lens body about an axis extending transverse to the central axis of the lens body for purposes of reducing its transverse dimension in at least one plane, thus facilitating storage in a sterile condition and container, and enabling delivery into the eye in such conformed condition. Enabling delivery of the hydrated hydrophilic lens assembly in a conformed reduced transverse dimension condition enables use of a significantly smaller incision or opening through which the conformed lens may be delivered into the eye, thus resulting in significantly less trauma to the patient. In one aspect of the invention, the hydrated hydrophilic lens assembly in conformed form is contained within a sterile tubular container sealed at both ends and enclosing the lens assembly in an appropriate saline solution. In another aspect of the invention, the hydrated hydrophilic lens assembly is enclosed within a tubular container open at both ends, with the tubular container contained within a saline solution-filled pouch. In still another aspect of the invention, the tubular member within which the hydrated hydrophilic lens assembly is conformed and retained forms part of a hypodermic-like instrument for insertion or delivery of the lens assembly into the eye.

DESCRIPTION OF THE PREFERRED EMBODIMENT

Figure 3:
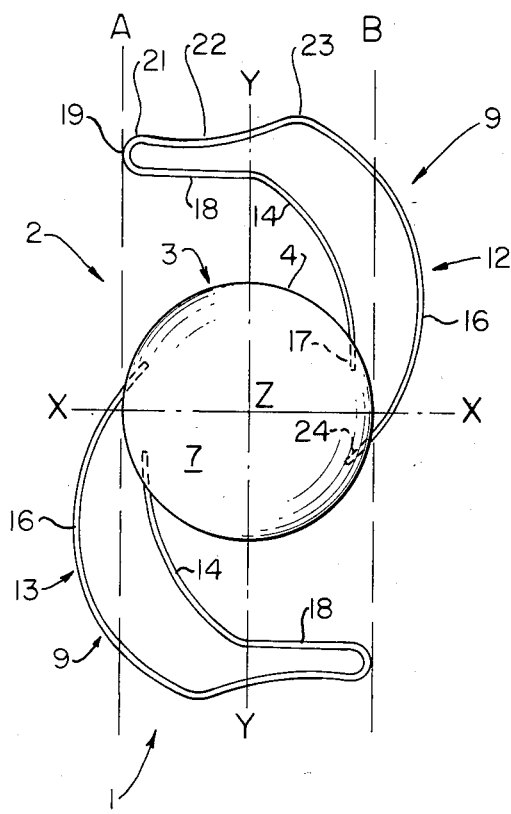
FIG. 3 is a front elevational view of the lens assembly shown apart from the eye.

In terms of greater detail, the hydrophilic intraocular lens assembly of the invention is adapted to be manufactured in a conventional manner, utilizing conventional equipment for manufacturing intraocular lenses, with the exception that the lens body and the support structure for the lens body are manufactured from a hydrophilic synthetic resinous material in dehydrated form which, when hydrated, absorbs approximately thirty to seventy percent by weight of water, thus causing the lens assembly to "grow" into its finished form. We have found that fabrication of the lens assembly may proceed utilizing equivalent hydrophilic synthetic resin materials such as polymacon, hefilcon A; vifilcon A; tetrafilcon A; dimefilcon A; droxifilcon; bufilcon A; ocufilcon; deltafilcon A; tetrafilcon A; etafilcon A; phemfilcon A; silafocon A; porofocon Al; perfilcon A; hefilcon B; lidofilcon B; crofilcon A; and tefilcon. These are believed to be the correct generic names for specific equivalent synthetic resinous materials from which lens assemblies may be fabricated. For instance, by way of example, we have found that a lens assembly fabricated from ocufilcon comprises the copolymer 2-hydroxyethylmethacrylate and methacrylic acid cross linked with ethylene glycol dimethacrylate. We have found that the ocufilcon, when compounded in ratios by weight of 0.4% ethylene glycol dimethacrylate and 2.1% methacrylic acid and the balance 2-hydroxyethylmethacrylate, produces a lens body that is sufficiently "soft" to permit it to be conformed about an axis that extends transverse to the central or optical axis of the lens.

By way of further example a lens assembly fabricated from the synthetic resin material polymacon comprises 2-hydroxyethyl methyl methacrylate polymer cross-linked with ethylene glycol dimethacrylate, while a lens assembly fabricated from hefilcon A comprises a copolymer of 2-hydroxethyl methacrylate and N-vinyl-2-pyrrolidone. Further, the synthetic resin vifilcon A comprises Poly (2-hydroxyethyl methacrylate-co-ethylene dimethacrlic acid-g-povidone); tetrafilcon A comprises a terpolymer of 2-hydroxyethyl methacrylate, methylmethacrylate and N-vinyl pyrrolidone; dimefilcon A comprises 2-hydroxyethyl methacrylate and methylmethacrylate polymer; droxifilcon comprises a random polymer of 2-hydroxethyl methacrylate and methacrylic acid modified with polvinyl-pyrrolidone; bufilcon A comprises a random copolymer of 2-hydroxethyl methacrylate, N-(1,1-dimethyl-3-oxobutyl)-acrylamide and methacrylic acid; deltafilcon A comprises a copolymer of (2-hydroxyethyl methacrylate)-(isobutyl methacrylate)-(trimethylolopropane trimethacrylate)-(methacrylic acid); etafilcon A comprises poly (2-hydroxyethyl methacrylate co-sodium metharylate-co 1,1,1 Trimethylol propane trimethacrylate); phemilcon A comprises a copolymer of 2-hydroxyethyl methacrylate, 2-ethoxyethylmethacrylate and methacrylic acid cross-linked with ethylene glycol dimethacrylate; and silafocon A comprises a copolymer of random cross-linked units derived from 3-[3,3,5,5,5,-pentamethyl-1,1-bis[pentamethyl disiloxany] oxy] trisiloxyanyl] propyl methacrylate, methyl methacrylate, methacrylic acid, and tetraethylene glycol dimethacrylate. Additionally, the resin material porofocon A comprises a polymer of cellulose acetate butyrate; perfilcon A comprises a terpolymer of 2-hydroxyethyl methacrylate, N-vinyl-2-pyrrolidone, and methacrylic acid with ethyleneglycol dimethacrylate as a cross-linking agent; hefilcon B comprises a copolymer of 2-hydroxyethyl methacrylate and N-vinyl-2-pyrrolidone; lidofilcon B comprises a copolymer of 1-vinyl-2-pyrrolidone and methyl methacrylate, with allyl methacrylate and ethylene dimethacrylate; crofilcon A comprises 2, 3-dihydroxypropyl methacrylate and methyl methacrylate cross-linked with ethylene glycol dimethacrylate; and tefilcon comprises a polymer of 2-hydroxyethylmethacrylate cross-linked with ethylene glycol dimethacrylate.

We have found that this material, formulated in the ratios indicated above, produces a lens body, or filamentary material for use in connection with the support structure of the lens body in the eye, which is sufficiently "soft" that it may be rolled or bent into a configuration in which the transverse dimension of the assembly is considerably reduced, thus permitting it to be inserted into the eye through a substantially smaller incision or opening (3.5 mm) than usual (6.5 mm). While the lens assembly, fabricated from ocufilcon as described above, or an equivalent hydrophilic resin, possesses the requisite "softness" to be rolled or bent nevertheless, the lens assembly also possesses sufficient "rigidity" or structural cohesiveness to be self-supporting in either the dehydrated or hydrated state.

Figure 4:
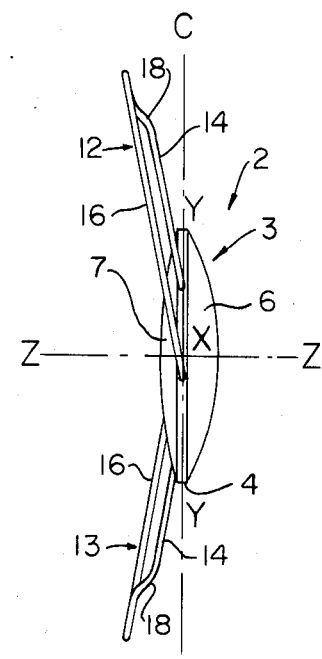
FIG. 4 is a side elevational view of the lens assembly shown apart from the eye.
Figure 1:
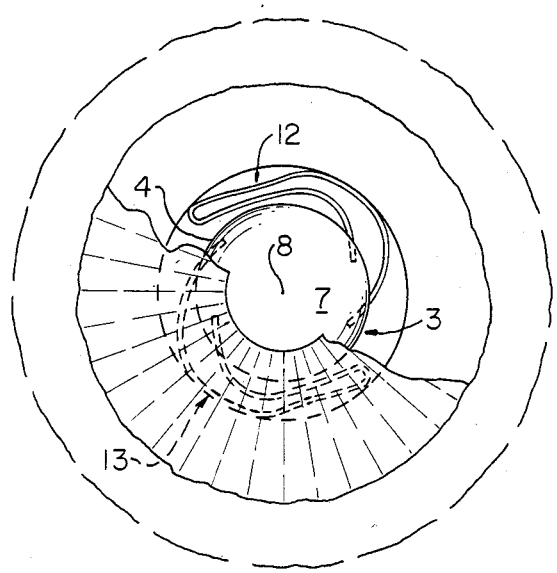
FIG. 1 is a fragmentary front elevational view showing the hydrophilic hydrated lens assembly in place in the capsular bag in the eye.
Figure 8:
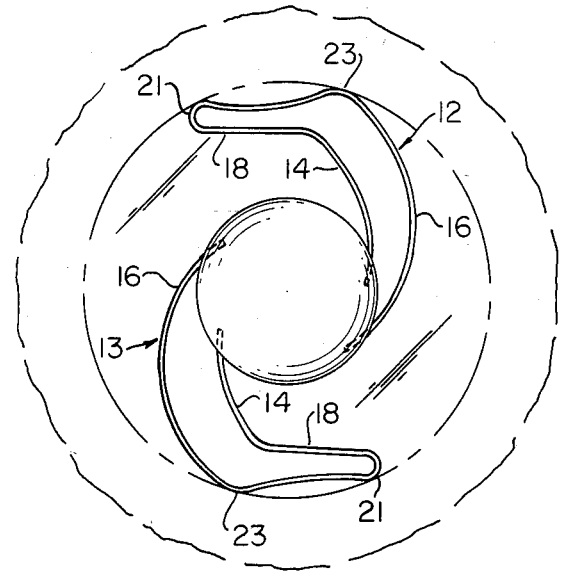
FIG. 8 is a fragmentray front elevational view of the lens assembly mounted as illustrated in FIG. 7.
Figure 7:
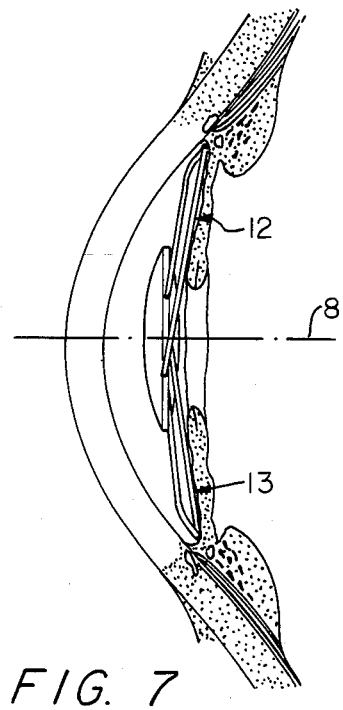
FIG. 7 is a fragmentary cross-sectional view illustrating the lens assembly of the invention mounted in the anterior chamber of the eye.
Figure 6:
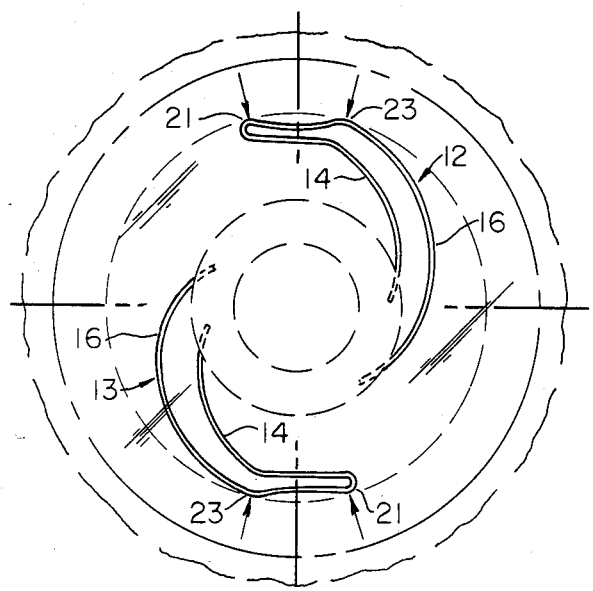
FIG. 6 is a fragmentary front elevational view illustrating the lens assembly of FIG. 5 mounted in the eye and supported out of the capsular bag.
Figure 5:
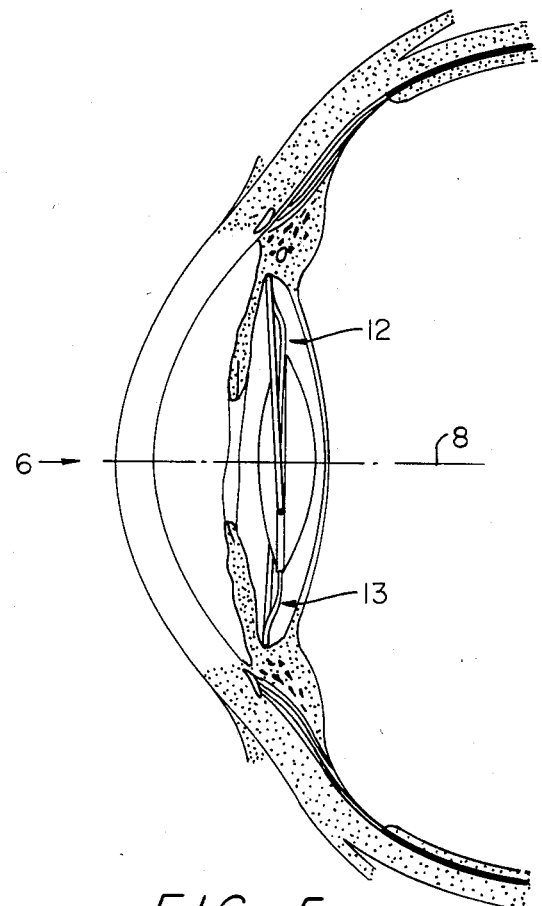
FIG. 5 is a fragmentary cross-sectional view through the optical axis of the eye illustrating the lens of the invention mounted in the posterior chamber of the eye, but out of the capsular bag.

While it is not desired to be limited to a specific configuration of lens body and supporting structure, we have found the configuration illustrated in the drawings, particularly FIGS. 3 and 4, to be especially useful in connection with a universally applicable posterior and anterior chamber lens assembly. It should be understood that while FIGS. 3 and 4 illustrate a lens assembly designed specifically for implantation in the posterior chamber of the eye, the configuration illustrated in FIGS. 7 and 8 is particularly adapted for implantation in the anterior chamber of the eye. It should be noted that with respect to the configuration of the lens assembly illustrated in FIGS. 3 and 4, the supporting members of the structure possess an anteriorly directed inclination, whereas with the anterior chamber lens assembly illustrated in FIGS. 7 and 8, the supporting structure, while otherwise corresponding in configuration to the lens assembly of FIGS. 3 and 4, is posteriorly directed or inclined as illustrated.

With respect to structure, and configuration of the lens assembly, and referring specifically to FIGS. 3 and 4, it will there be seen that the lens assembly designated generally by the numeral 2 is defined with respect to an X-axis, a Y-axis, a Z-axis, and planes A, B, and C. As illustrated in FIGS. 3 and 4, the X-axis extends transversely across the lens, intersecting the Z-axis which is coincident with the optical axis of the lens, while the Y-axis intersects both the X and Z axes and extends transverse to the lens perpendicular to the X-axis.

Further, plane A as viewed in FIG. 3 is tangent to the left periphery of the lens as there illustrated, while plane B is tangent to the right periphery of the lens, plane C being perpendicular to both planes A and B and including the equatorial rim of the lens body and the X and Y axes, while being perpendicular to the Z-axis. In like manner, planes A and B are perpendicular to the X-axis and parallel to the Y and Z axes.

With these spacial relationships in mind, reference being had to FIGS. 3 and 4, it will be seen that the lens assembly comprises a lens body designated generally by the numeral 3, having an outer circular periphery 4 generally symmetrical about the Z-axis and having a diameter of approximately 6 mm. The outer periphery 4 defines the equatorial rim or periphery of the lens body 3, with the posterior surface 6 of the lens body being spherical in configuration but having a shorter radius than the spherical surface 7 forming the anterior surface of the lens body 3. Thus, the lens illustrated in FIGS. 3 and 4 constitutes a convex - convex lens. It should be understood however, that the lens body may be a planoconvex lens in appropriate circumstances.

Figure 2:
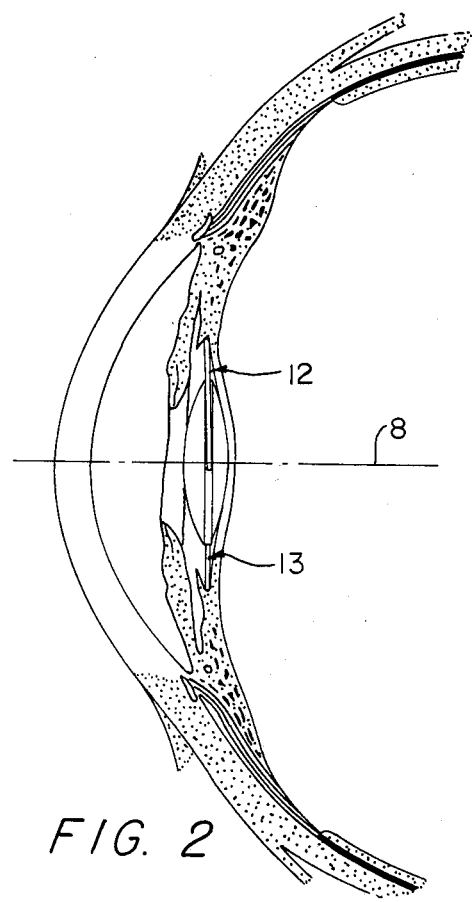
FIG. 2 is a fragmentary cross-sectional view through the optical axis of the eye and showing the lens assembly of the invention in place in the capsular bag.

It is one of he objects of the invention to support the lens body 3 centrally disposed within the eye so that the optical axis Z of the lens body coincides with the optical axis of the eye, represented in FIG. 2 by the line 8. To thus support the lens body 3, there is provided a plurality of support members designated generally by the numeral 9 and generally disposed symmetrically with respect to the X, Y and Z axes. Thus, referring to FIG. 3, two such support members are provided, designated by the numerals 12 and 13, respectively. Each of the support members 12 and 13 are identical in configuration but are mounted in substantially diametrically opposed positions with respect to the lens body 3. We have found that fixation of the lens assembly within the eye is best accomplished when the point of attachment of the resiliently flexible support members 12 and 13 to the periphery 4 of the lens body 3 occurs at locations substantially diametrically opposed and associated with the X-axis as illustrated in FIG. 3. Fixation of the lens assembly in the eye is enhanced when the support members 12 and 13 are resilient in nature, and project radially outwardly and circumferentially about the lens to provide flexibly resilient lens body support portions diametrically opposed and spaced from the periphery of the lens body in the direction of the Y-axis a distance greater than one-half the transverse dimension of the lens body when in relaxed condition as illustrated in FIGS. 3 and 4. Additionally, it has been found to be advantageous to form each support member from an elastically flexible resiliently deformable synthetic resin filament, which may be hydrophilic, but which is crescentiform in its configuration to form a loop having distinct portions thereof in contact with the support structure of the eye, these support portions of the loop being equidistant from the Z-axis of the lens and being formed integrally with the elastically flexible and resiliently deformable crescentiform loop of synthetic resinous filamentary material.

Thus, in greater detail, and referring to FIG. 3, and specifically to the support member 12, it will be seen that the support member 12 is provided with inner and outer legs 14 and 16, respectively. The inner leg 14 is curved in its free configuration commencing from its anchor portion 17, which is embedded in the peripheral portion of the lens body substantially parallel to the B-plane and positioned on one side of the X-axis. Leg 14 extends away from the periphery 4 in an arc that approaches the Y-axis, where the curved leg 14 joins integrally with a leg extension 18 that is straight and lies substantially perpendicular to the Y-axis and the A and B planes and which joins integrally a circularly formed end portion 19 having a peripheral contact portion 21 next adjacent the integral union of the circular portion 19 with a curved intermediate leg portion 22. Intermediate leg portion 22 is concave in a direction away from the lens body 3, and joins integrally with a contact portion 23 which in turn merges integrally and smoothly with the outside leg 16. This leg is also curved in its configuration, being concave in a direction toward the lens body, and the terminal portion 24 of this leg 16 is embedded in the peripheral portion of the lens body at a point below the X-axis, on the opposite side thereof from the anchor portion 17 of the inside leg 14.

From this lens assembly configuration, it will be seen that the support members lend themselves to use universally in supporting the lens assembly in the capsular bag, which is somewhat smaller in diameter than the sulcus, or supporting the assembly in the sulcus in the posterior chamber of the eye or, alternatively, supporting the lens assembly in the anterior chamber of the eye with the support members engaging the anterior angle. Because of its crescentiform configuration, the various parts of the support member cooperate one with the other so that the contact points 21 and 23 are spaced equidistant from the central or optical axis Z, regardless of the diameter of the environment in which the lens assembly is supported. Thus, from the configuration illustrated in FIG. 3, which is the relaxed condition of the supporting members, radially inwardly directed pressure on contact portions 21 and 23 will cause both the legs 14 and 16, which are already curved, to increase their curvature, i.e., to curve about a shorter radius, while maintaining the relationship of the contact portions 21 and 23 with the optical axis of the lens. In this manner the contact portions exert equal pressure outwardly against the supporting eye structure, whether it be the capsular bag, the posterior chamber sulcus, or the anterior chamber angle.

As illustrated in FIG. 4, the two support members 12 and 13 are inclined anteriorly, i.e., toward the anterior chamber of the eye when it is intended that the lens assembly be implanted in the posterior chamber of the eye. Thus, the support members 12 and 13 are angled away from the C-plane in the direction of the Z or optical axis. It should be understood that for implantation in the anterior chamber of the eye, depending upon the configuration of the lens body itself, the supporting members 12 and 13 may be inclined posteriorly so as to appropriately engage the anterior chamber angle of the eye and properly position the lens body 3 in front of the iris with at most very slight contact with the edges of the iris in its most contracted condition. It should also be noted that the contact portions 21 and 23 of each of the support members 12 and 13 are preferably aligned in a common circumferential plane. To accomplish this, the extension portion 18 of the inner leg 14 is offset posteriorly as indicated in FIG. 4.

Obviously, it is extremely important that once the lens assembly is implanted in the eye, whether it be implanted in the capsular bag, in the posterior chamber sulcus, or in the anterior chamber of the eye, it be fixed against dislocation in which the optical axis of the lens body is displaced laterally or vertically with respect to the optical axis of the eye. Many different support structures have been devised in the past in an attempt to accomplish this purpose. For many reasons, many of these support structures have failed to solve the problem. It is believed that the structure illustrated and described herein solves this problem to a high degree in that with only two support structures, the lens assembly is prevented from shifting or dislocating transversely, vertically, or axially within the eye. This is accomplished through use of the crescentiform support members 12 and 13, each of which is attached to the periphery of the lens body 3 at diametrically opposite peripheral portions associated with the X-axis of the lens, with anchor portions 17 and 24 on opposite sides of the X-axis. Each of the crescentiform support members 12 and 13 then extends radially outwardly and circumferentially so as to place the two contact portions 21 and 23 on opposite sides of the Y-axis, and diametrically opposed to the corresponding support members on the opposite side of the X-axis. Thus, any tendency of the lens body 3 to move from left to right or from right to left as viewed in FIGS. 1, 3, 6 and 8 is resisted by the support members 12 and 13, specifically those portions of the inner and outer legs 14 and 16 next adjacent the periphery of the lens body and associated with the X-axis. In like manner, movement of the lens body vertically in the direction of the Y-axis is resisted by the legs 14 and 16, since any such movement of the lens body would tend to place these members in compression or to increase their curvature, thus encountering a force counteracting movement of the lens body in a vertical plane. Because the support legs 14 and 16 are both curved and resiliently flexible, they may be compressed into a smaller diameter without causing the lens body to vault forward. This is particularly important with an anterior chamber lens because it precludes the lens vaulting forward, thus avoiding contact with the cornea. Another major advantage of the curved support legs is that they minimize contact with the anterior angle structure and thus minimizes anterior angle irritation, which, if permitted to persist, may be manifested by a peculiar neovascular scarring that causes fibrosis to the iris and distorts the pupil.

In FIG. 3 and 4, the supporting members 12 and 13 are illustrated as formed from an elastically flexible and resiliently deformable synthetic resin filament. This filament may be fabricated from polypropylene or it may be fabricated from a hydrophilic filamentary material which may be the same material from which the lens body is fabricated.

Figure 9:
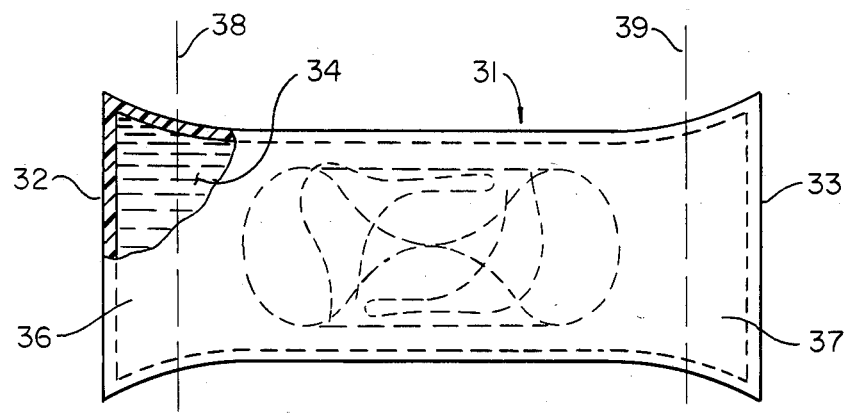
FIG. 9 is an elevational view illustrating the lens assembly of the invention sealed within a tubular container filled with an appropriate saline solution to hydrate the lens.

We have found that when the lens body 3 is fabricated from a hydrophilic material which is hydrated to within the preferred range of approximately 30 to 70% water content by weight, the lens assembly may be conformed (rolled, folded or bent) about a transverse axis, either the X-axis or the Y-axis as illustrated in FIG. 3, and the conformed lens assembly inserted into a capsule designated generally by the numeral 31 in FIG. 9. The capsule 31 is preferably fabricated from a transparent plastic material that may be heat sealed or adhesively sealed along the end edges 32 and 33 following insertion of the conformed lens assembly in the capsule. Prior to sealing, the capsule is filled with an appropriate saline solution 34 which effectively retains the lens hydrated until such time as the lens assembly is removed from the capsule and delivered into the eye. It will of course be understood that the capsule 31 is sterile, as is the lens assembly that is inserted thereinto, and that the sterile condition of the lens assembly is maintained during storage. The exterior of the sealed capsule, may be sterilized by any convenient method, and the sterile and sealed capsule then stored within any type of a container that will maintain the capsule in sterile condition.

To gain access to the sterile lens assembly contained within the saline-filled capsule 31, the end portions 36 and 37 are snipped off at the cutting planes 38 and 39, respectively, thus opening both ends of the tubular capsule 31 so that the lens assembly may be ejected therefrom by an appropriate probe (not shown). It should be understood that the tubular capsule 31 has an exterior diameter of approximately 3.5 mm, with the lens assembly within the tubular capsule being rolled snugly therewithin. Thus, the tubular capsule 31 may be utilized as a channel to inject the lens assembly through the opening into the eye, thus facilitating delivery of the lens assembly into the eye. In this procedure, the now open-ended tubular capsule 31, being sterile, is inserted through the opening created by the opthamologist and the lens assembly is pushed from the rear into the approximate position that it is to occupy within the eye. The tubular delivery tube 31 is then removed, and the opthamologist proceeds with extension and proper positioning of the lens assembly within the eye.

Figure 10:
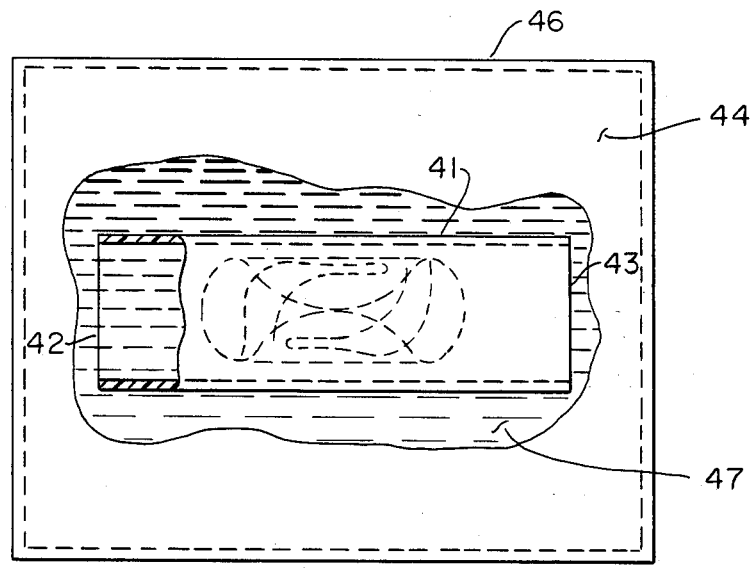
FIG. 10 is a plan view illustrating the lens assembly of the invention conformed within the interior of a tubular capsule open at both ends and which tubular capsule is in turn sealingly enclosed within a saline-filled pouch.

The enclosure and conformation of the lens assembly within the interior of a plastic delivery tube lends itself to delivery of the lens assembly into the eye in several different ways using several different means. Reference is made to FIG. 10 of the drawings. As there shown, the lens assembly is enclosed within an open-ended plastic tube designated generally by the numeral 41 and including open ends 42 and 43. The plastic tube 41 is preferably relatively rigid, may be completely cylindrical, or may be ovate in its cross-sectional configuration, so as to accommodate the rolled up lens assembly therewithin. In this embodiment of the invention, the plastic tube 41 functions to retain the lens assembly in rolled-up conformed condition, and this entire assembly of plastic tube 41 and lens assembly is then sealed within a liquid-tight pouch 44 that may be fabricated from any appropriate material, including plastic, and which has its peripheral edges 46 sealed against the entry of air or the egress of a saline solution 47 which fills the interior of the pouch 44.

Thus, the saline solution passes through the open ended tube 41, surrounding the lens assembly, and effectively retaining it in a hydrated condition until such time as the lens assembly is to be used. One of the advantages of maintaining the lens assembly in hydrated condition, is that it is maintained in a sterile condition, and that the saline solution within which it is stored is compatible with the natural fluids found in the eye. Thus, the delivery procedure is simplified in that the capsule 31 or the pouch 44 need only be opened and the capsule 31 or the tube 41 utilized as an instrument of delivery of the lens assembly into the eye.

Figure 11:
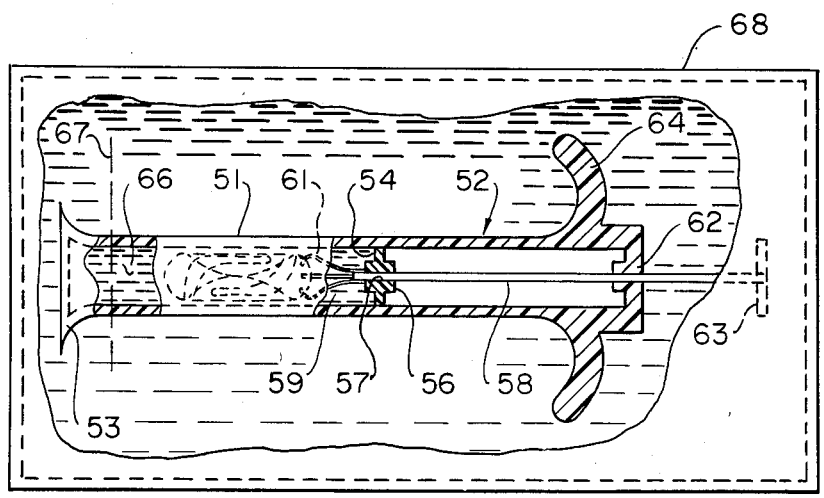
FIG. 11 is a vertical cross sectional view taken through the central axis of a hypodermic-like device which functions to contain the lens assembly of the invention in conformed condition and which assists in delivery of the lens assembly into the eye.

In the embodiment of the invention, illustrated in FIG. 11, the intraocular lens assembly is enclosed within the tubular barrel 51 of a hypodermic-type instrument designated generally by the numeral 52, formed from an appropriate plastic. In the illustration of FIG. 11, the terminal end 53 of the tube 51 has been crimped and sealed so as to completely enclose the lens assembly therewithin. Intermediate the ends of the instrument 52, there is provided a diametrically extending bearing wall 54 having a reinforced central section 56 through which extends an axial bore 57 adapted to slideably receive a plunger rod 58. On the inner end of the plunger rod 58 which extends into the interior chamber 59 of tube 51, the plunger rod is provided with a plurality of fingers 61 that extend radially outwardly from the rod end and are adapted to engage the rolled-up lens assembly contained within the tube 51.

The opposite end of the plunger rod 58 is slidably received in the end capsule 62 and is provided with a head 63 which cooperates with the finger grip portions 64 to permit digital manipulation of the plunger rod 58. Thus, the interior 59 of the tube 51 is filled with a saline solution 66 to maintain the lens assembly hydrated, and when it is desired to use the lens assembly, all that is required is that the end of the tube 51 be snipped off along the cutting line 67 to thus expose and open the end of the tube 51. After the saline solution has been drained from the tube 51, the plunger 58 may be manipulated so that the lens assembly may be ejected from the interior of the tube 51. Preferably, the hypodermic-type instrument 52 is completely sterilized inside and out prior to insertion of the lens assembly within the tube 51 and the injection of the saline solution thereinto. The entire sterile hypodermic-type instrument 52 and enclosed lens assembly is preferably then enclosed in a sterile package 68 indicated generally by the broken lines in FIG. 11.

The sterile package 68 may be in the form of a sealed pouch which itself is filled with a saline solution in the same manner as illustrated and discussed in connection with the embodiment of FIG. 10. When the sterile container 68 constitutes a saline-filled pouch, it will of course be understood that the end portion 53 of the tube 51 need not be sealed, and may be left open in the same manner that the tube 41 illustrated in FIG. 10 is left open. Thus, the tubular member 51 being sterile, this portion of the hypodermic-type instrument may be inserted through the relatively small 3.5 mm opening created by the surgeon so as to place the open end of the tube very close to the location where the surgeon wishes to deposit the lens assembly. The plunger 58 is then manipulated so as to inject the lens assembly into the eye, and the instrument is withdrawn, whereupon the surgeon may extend and position the lens assembly within the eye.

From the above, it will be apparent that we have provided a "soft" intraocular lens assembly that opens up several avenues for improvement in the procedure for the implantation of intraocular lenses in the human eye. Additionally, the combination of a "soft" material from which the lens assembly is fabricated and the packaging within which it is retained in a sterile condition and which serves to assist in the delivery of the sterile lens assembly into the eye, reduces the time that the surgeon remains in the patient's eye, thus reducing trauma to the patient and rendering the entire procedure more economical, thus benefitting the patient.

While we have specifically identified ocufilcon as being a suitable material from which the lens body 3 and the support structures may be fabricated, it should be understood that the other materials also identified are considered to be the full equivalent of ocufilcon and may be substituted therefor. As indicated above, the ocufilcon comprises the copolymer 2-hydroxyethylmethacrylate and methacrylic acid cross-linked with ethylene glycol dimethacrylate. In like manner, the equivalent hydrophilic resins identified above possess equivalent physical properties which accommodate hydration of the lens assembly to a degree of approximately 30 to 70% by volume, and which are rendered "soft" to the extent that the lens assembly, including the supporting structure, may be conformed about a transverse axis of the lens body so as to form a compact unit that may be inserted into the eye in such compact condition. It is of course understood that the physical properties of the resins or polymers of the invention are controlled by controlling the ratios of the modifiers and the crosslinking agents to the amount of the total polyer used in the reaction mixture. These ratios vary generally only a small amount from the ratios discussed above in connection with ocufilcon.

It is further understood that the properties of the optically transparent lens body can be modified by the addition, to any of the above-listed resin materials, of an ultraviolet filter compound which includes 3-(2 Benzyotriazolyl)-2-Hydroxy-5-Tert-Octyl-Benzyl Methacryl Amide.

Having thus described the invention, what is believed to be new and novel and sought to be protected by Letters Patent of the United States is as follows:

We claim:

1. An intraocular lens assembly for implantation in the human eye so that the optical Z axis of said lens assembly is coincident with optical axis of the eye when implanted comprising:

(a) an optically transparent lens body formed from a hydrophilic synthetic resin material and having a transverse dimension defining an outer periphery disposed about said optical Z axis, said outer periphery lying in a vertical plane perpendicular to said optical Z axis, said lens having X and Y axes lying in said vertical plane and mutually perpendicular to each other;

(b) a pair of resilient support members attached to said lens body at diametrically opposed attachment locations adjacent corresponding opposed intersections of said X-axis with said periphery of said lens body, said resilient support members projecting radially outwardly and extending circumferentially about said lens body in the direction of said Y-axis to provide resilient lens-body support portions which are diametrically opposed and which are spaced from the periphery of said lens body a distance greater than one-half the transverse dimension of said lens body; and (c) first and second contact portions formed on at least one of said resilient support portions extending radially outwardly from said optical Z axis a distance greater than the remainder of said support portion, said first contact portion lying on the opposite side of said Y-axis from said second contact portion.

2. The combination according to claim 1, in which said support members are formed from elastically flexible resiliently deformable synthetic resin filaments.

3. The combination according to claim 1, in which said first and second contact portions are spaced equidistant from the optical (Z) axis of said lens body.

4. The combination according to claim 1, in which said support members extend anteriorly in the direction of said Z-axis, said support portions lying anteriorly of said vertical plane including said X and Y axes.

5. The combination according to claim 1, in which said support members are formed from hydrophilic synthetic resin filamentary material.

6. The combination according to claim 1, in which said pair of support portions lie in a common plane spaced anteriorly of said vertical plane including said X and Y axes.

7. The combination according to claim 1, in which each of said support members comprises an elastically flexible and resiliently deformable crescentiform loop of synthetic resinous filamentary material.

8. The combination according to claim 1, in which each said support member is formed from a length of synthetic resin filamentary material having first and second ends and configured to have a crescentiform loop shape said first and second ends of said filament being attached to the periphery of the lens body at circumferentially spaced locations on opposite sides of the corresponding intersection of said X-axis with said periphery, said loop having an intermediate portion forming said first and second contact portions.

9. The combination according to claim 1, in which a portion of each said support member extends radially outwardly in the direction of the X-axis and lies outside a vertical plane tangent to the associated peripheral portion of the lens body and parallel to the Y-axis, said support member extending circumferentially from its point of attachment to the lens body on one side of the Y-axis to a point spaced from the lens body on the other side of the Y-axis.

10. The combination according to claim 1, in which said lens body is circular and said lens body periphery is concentrically disposed about said optical (Z) axis.

11. The combination according to claim 1, in which said intraocular lens assembly is adapted for implantation in the natural lens capsule of the human eye, and said pair of support members are adapted to engage the lens capsule to support the lens body therewithin.

12. The intraocular lens assembly for implantation in the human eye according to claim 1 wherein said lens body is formed from a hydrophilic synthetic resin material formulated to accommodate, when hydrated, non-planar conformation of the lens body about an axis extending transverse to the central axis of the lens body prior to implantation in the eye and extension of the lens body into supported position after implantation.

13. The combination according to claim 12, in which said hydrophilic synthetic resin material is formulated when hydrated to accommodate rolling of the lens body about an axis extending transverse to the central axis of the lens body.

14. The combination according to claim 12, in which said support members extend from the periphery of the lens in the direction of said transversely extending axis, whereby when said lens body is conformed thereabout in a non-planar configuration the support members extend from opposite ends of the conformed lens body.

15. The combination according to claim 12, in which said support members extend from the periphery of the lens in a direction perpendicular to said transversely extending axis, whereby when said lens body is conformed thereabout the support members lie wrapped about said transversely extending axis.

16. The combination according to claim 12, in which at least one of said support members comprises an elastically deformable loop whereby when said assembly is implanted in the eye said loop engages the eye in cooperation with said other support member to center the lens in the eye.

17. The combination according to claim 12, in which said intraocular lens assembly is adapted for implantation in the natural lens capsule of the human eye, and said support members are adapted to engage the lens capsule to support the lens body whereby the central axis of the lens coincides with the optical axis of the eye.

18. The combination according to claim 12, in which said resin material comprises 2-hydroxyethyl methyl methacrylate polymer cross-linked with ethylene glycol dimethacrylate.

19. The combination according to claim 12, in which said resin material comprises a copolymer of 2-hydroxyethyl methacrylate and N-vinyl-2-pyrrolidone.

20. The combination according to claim 12, in which said resin material comprises Poly (2-hydroxyethyl methacrylate-co-ethylene dimethacrylic acid-g-povidone).

21. The combination according to claim 12, in which said tetrafilcon A comprises a terpolymer of 2-hydroxyethyl methacrylate, methylmethacrylate and N-vinyl pyrrolidone.

22. The combination according to claim 12, in which said resin material comprises 2-hydroethyl methacrylate and methylmethacrylate polymer.

23. The combination according to claim 12, in which said droxifilcon comprises a random polymer of 2-hydroxethyl methacrylate and methacrylic acid modified with polyvinylpyrrolidone.

24. The combination according to claim 12, in which said resin material comprises a random copolymer of 2-hydroxethyl methacrylate, N-(1, 1-dimethyl-3-oxobutyl)-acrylamide and methacrylic acid.

25. The combination according to claim 12 in which said resin material comprises the copolymer 2-hydroxyethyl methacrylate and methacrylic acid cross-linked with ethylene glycol dimethacrylate.

26. The combination according to claim 12, in which said resin material comprises a copolymer of (2-hydroxyethyl methacrylate)-(isobutyl methacrylate)- (trimethylolopropane trimethacrylate)-(methacrylic acid).

27. The combination according to claim 12, in which said resin material comprises poly (2-hydroxyethyl methacrylate co-sodium methacrylate-co 1,1,1 Trimethylol propane trimethacrylate).

28. The combination according to claim 12, in which said resin material comprises a copolymer of 2-hydroxyethyl methacrylate, 2-ethoxyethylmethacrylate and methacrylic acid cross-linked with ethylene glycol dimethacrylate.

29. The combination according to claim 12, in which said resin material comprises a copolymer of random cross-linked units derived from 3-[3,3,5,5,5,-pentamethyl-1,1-bis[pentamethyl disiloxany) oxy] trisiloxanyl] propyl methacrylate, methyl methacrylate, methacrylic acid, and tetraethylene glycol dimethacrylate.

30. The combination according to claim 12, in which said resin material comprises a polymer of cellulose acetate butyrate.

31. The combination according to claim 12, in which said resin material comprises a terpolymer of 2-hydroxyethyl methacrylate, N-vinyl-2-pyrrolidone, and methacrylic acid with ethylene glycol dimethacrylate as a cross-linking agent.

32. The combination according to claim 12, in which said resin material comprises a copolymer of 2-hydroxyethyl methacrylate and N-vinyl-2-pyrrolidone.

33. The combination according to claim 12, in which said resin material comprises a copolymer of 1-vinyl-2-pyrrolidone and methyl methacrylate, with allyl methacrylate and ethylene dimethacrylate.

34. The combination according to claim 12, in which said resin material comprises 2, 3-dihydroxypropyl methacrylate and methyl methacrylate cross-linked with ethylene glycol dimethacrylate.

35. The combination according to claim 12, in which said resin material comprises a polymer of 2-hydroxyethylmethacrylate cross-linked with ethylene glycol dimethacrylate.

36. The combination according to claim 1 or 12 in which said hydrophilic lens body comprises approximately from 30% to 70% water by weight when hydrated.

37. The combination according to claim 26, in which the ratios by weight of said ingredients are 0.4% ethylene glycol dimethacrylate; 2.1% methacrylic acid and the balance 2-hydroxyethyl methacrylate.

38. The combination according to claims 1 and 12 in which said optically transparent hydrophilic lens body constitutes a filter to ultra violet light.

39. The combination according to claim 38, in which said optically transparent hydrophilic lens body includes 3-(2-Benzyotriazolyl)-2-Hydroxy-5-Tert-Octyl-Benzyl Methacryl Amide.

40. The combination according to claims 1, or 12, in which said optically transparent hydrophilic lens body comprises a soft, flexible, formable mass which may be folded or rolled about an axis transverse to the central optical axis of the lens body.

41. The combination according to claim 1, 13, 18, 19, 20, 21, 22, 23, 24, 25, 26, 27, 28, 29, 30, 31, 32, 33, 34 or 35, in which an ultra violet filter compound consisting of 3-(2-Benzyotriazolyl)-2-Hydroxy-5-Tert-Octyl Benzyl Methacryl Amide is added to said optically transparent hydrophilic lens material.

* * * * *